United States Patent [19]

Harm et al.

[11] Patent Number: 4,722,902
[45] Date of Patent: Feb. 2, 1988

[54] APPARATUS AND METHOD FOR CULTURING CELLS, REMOVING WASTE AND CONCENTRATING PRODUCT

[75] Inventors: William H. Harm, Columbia Heights; Mark D. Hirschel, Blaine; Michael L. Gruenberg, Coon Rapids, all of Minn.

[73] Assignee: Endotronics, Inc., Coon Rapids, Minn.

[21] Appl. No.: 794,627

[22] Filed: Nov. 4, 1985

[51] Int. Cl.$^4$ .............................................. C12M 3/00
[52] U.S. Cl. .................................... 435/284; 435/311
[58] Field of Search ............... 435/284, 285, 286, 311, 435/313, 316, 290, 291, 813; 210/137, 321.2, 321.3, 433.2

[56] References Cited

U.S. PATENT DOCUMENTS

| | | | |
|---|---|---|---|
| 3,883,393 | 5/1975 | Knazek et al. | 435/284 |
| 3,992,301 | 11/1976 | Shippey et al. | 210/433.2 |
| 4,420,398 | 12/1983 | Castino | 210/641 |

Primary Examiner—Samuel Scott
Assistant Examiner—Noah Kamen
Attorney, Agent, or Firm—Kinney & Lange

[57] ABSTRACT

An apparatus and method for culturing cells includes a waste removal and product concentrating loop in which waste is removed from the medium and product produced by the cells is concentrated for harvesting. The apparatus includes a reservoir for retaining a supply of medium. The reservoir is in fluid communication with a cell culturing loop wherein medium flows from the reservoir to the cells and back to the reservoir. The medium waste removal and concentrating loop removes waste components produced by the cells and is in fluid communication with the reservoir such that medium is transferred from the reservoir to the waste removal and concentrating loop and back to the reservoir. The waste removal and concentrating loop includes a device having a semipermeable membrane. The medium flows along one side of the membrane for selective transfer of the waste components through the membrane. A mechanism for selectively producing a back pressure in the medium is included downstream of the membrane and aids in transfer of waste components through the membrane to remove the waste components from the medium.

18 Claims, 4 Drawing Figures

APPARATUS AND METHOD FOR CULTURING CELLS, REMOVING WASTE AND CONCENTRATING PRODUCT

BACKGROUND OF THE INVENTION

1. Field of the Invention.

The present invention relates to a method and apparatus for the culturing of cells, and in particular, it relates to a method and apparatus wherein the waste produced by the cultured cells is removed from the medium and preferably product produced by the cells is concentrated for harvesting.

2. Description of the Prior Art.

Perifusion culturing systems for the culturing of cells in-vitro are well known. The cells are fed nutrients and other factors using medium which is transported into a culturing chamber housing the cells and then is transported from the culturing chamber. The medium which contains nutrients and other factors is expensive and consequently such systems recirculate the medium since nutrients and other factors in the medium are not completely used in a single pass through the culturing chamber.

In addition to using the nutrients and other factors in the medium, the cells secrete waste products, such as lactic acid, into the medium. Over a period of time, the concentration of lactic acid builds up and has a deleterious effect on the cells. Waste products may inhibit a desired function, promote an undesired function, degrade or consume the product produced, or "kill" the cells or do all of the above or any combination of the above.

Typically, in the prior art systems, a batch exchange process is performed manually to replenish the medium with nutrients and other factors. Any product that was produced by the cells (which had been released into the medium) is separated from the medium by removing the medium and then performing a separate process to harvest the product. The process of removing the product is costly and time-consuming.

SUMMARY OF THE INVENTION

The present invention includes a method and an apparatus for culturing cells, removal from the medium waste products produced by the cells, and, if a useful product is produced by the cells, concentrating the product within the medium for harvesting. The apparatus includes a reservoir for retaining a supply of medium. A cell culturing loop in fluid communication with the reservoir includes means for pumping the medium from the reservoir through the cell culturing loop. Waste products produced by the cells and any useful products produced by the cells are released into the medium and the medium is returned to the reservoir. A waste removal and product concentration loop is in fluid communication with the reservoir. The waste removal and concentration loop includes a device having a semipermeable membrane. The medium flows along one side of the membrane so that waste products transfer across the membrane while any useful products produced by the cells are retained in the medium. The waste removal and concentration loop also includes a mechanism for producing a back pressure in the medium along the one side of the membrane to aid in the transfer of waste products from the medium through the membrane.

In use, the cells are cultured by recirculating the medium from the reservoir through the cell culturing loop. When a build up of waste component occurs in the medium, medium is drawn through the waste removal and concentration loop from the reservoir and is passed alongside the membrane for the transfer of waste components from the medium. The mechanism to provide a back pressure is activated to further aid in the transfer of waste components from the medium. Any useful higher molecular weight products are kept within the medium. The cycle described above is continued until the desired degree of concentration has occurred. Fresh medium is added in the waste removal and concentration loop to replenish the medium removed and the higher molecular weight components and useful products are flushed back to the reservoir. During this phase, the back pressure mechanism is adjusted so as to stop the concentrating process and allow higher flow rates through the concentration loop to help in flushing any lodged higher molecular weight components or useful product.

DETAILED DESCRIPTION OF THE PREFERRED EMBODIMENTS

Figure 1:
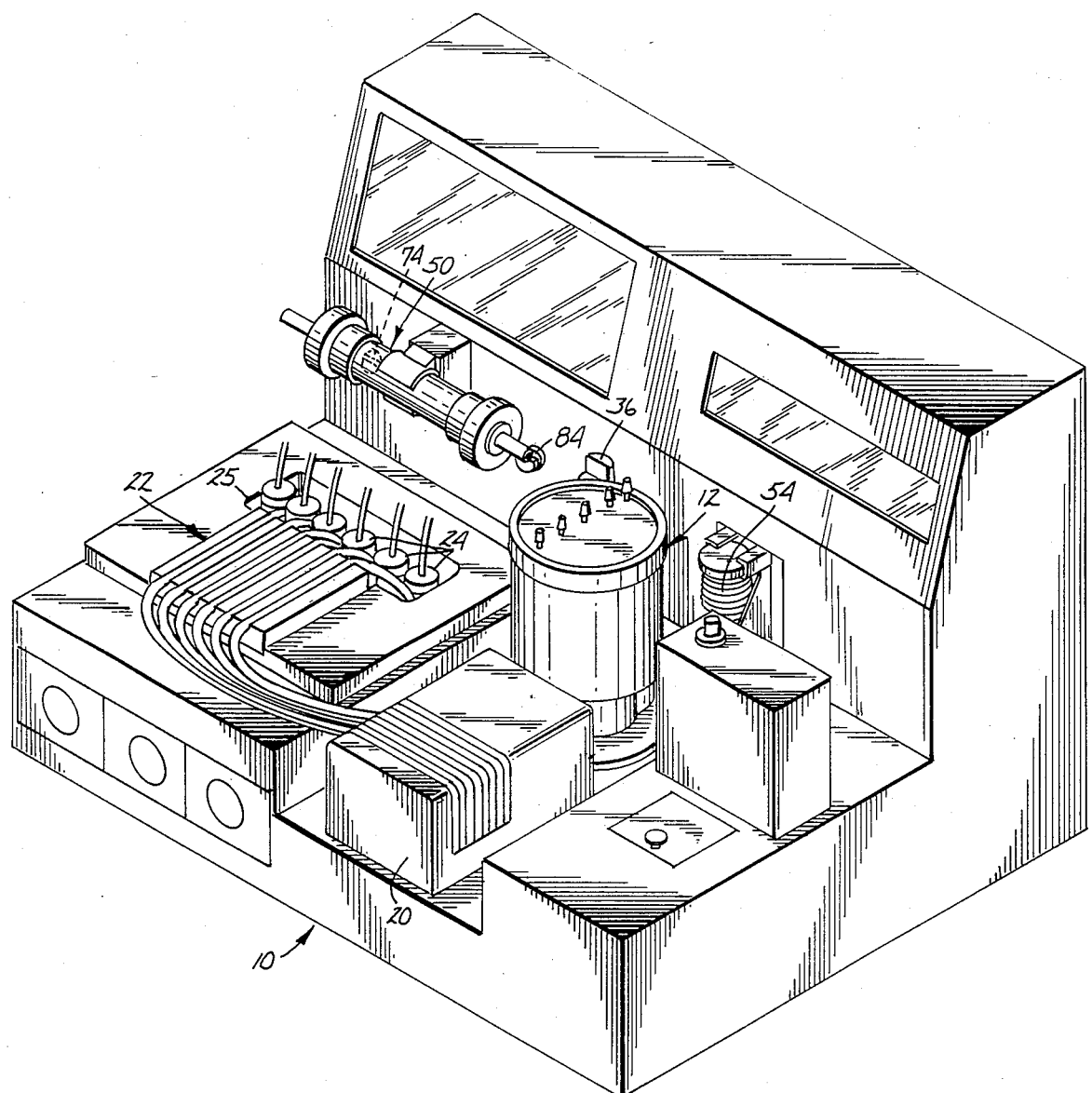
FIG. 1 is a perspective view of the apparatus of the present invention.
Figure 2:
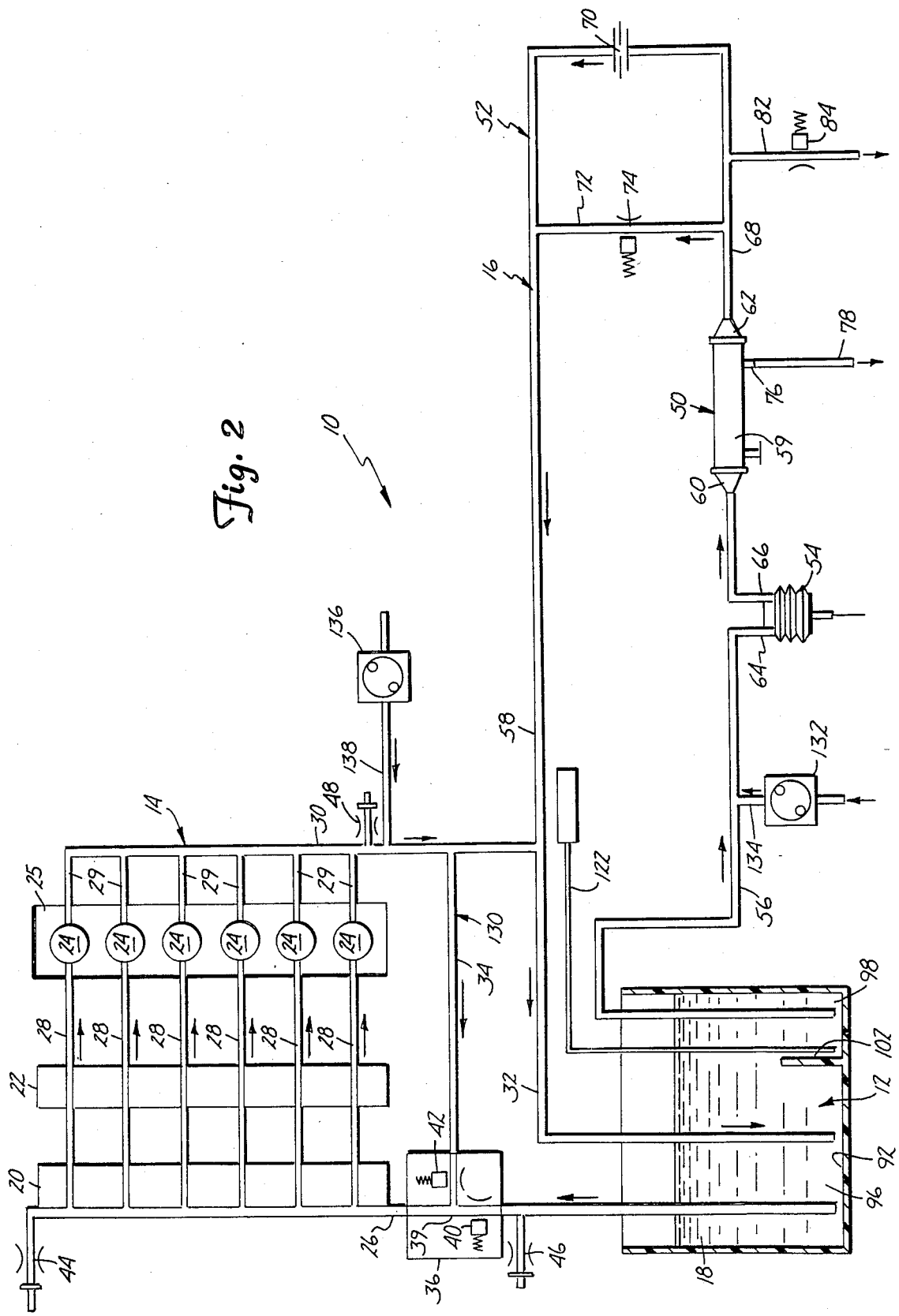
FIG. 2 is a diagrammatical view of the present invention.

A preferred embodiment of the apparatus of the present invention is generally indicated at 10 in a perspective drawing in FIG. 1 and a diagrammatical view in FIG. 2. The perspective view of FIG. 1 does not show all of the elements of the apparatus. FIG. 1 is included to illustrate a preferred physical arrangement of certain elements of the apparatus 10. The apparatus 10 includes a reservoir 12, a cell culturing loop 14 and a medium waste removal and concentrating loop 16, as best illustrated in FIG. 2. The reservoir 12 retains or holds a supply of medium 18 which is used to perifuse cells that are being cultured in the culturing loop 14.

The present invention is not limited to the specific embodiment of the culturing loop illustrated in FIGS. 1 and 2, and any recirculation-type culturing system that draws medium from the reservoir 12 and returns medium to the reservoir 12 after the cells have been perifused is includable within the scope of the present invention. The culturing loop 14, diagrammatically illustrated in FIG. 2 and partially illustrated in perspective in FIG. 1, is also described in U.S. patent application Ser. No. 658,548, filed on Oct. 9, 1984 by Harm et al and assigned to the same assignee as the present application and which is hereby incorporated by reference.

The cell culturing loop 14 includes a multiple channel pumping section 20, a heating and gassing section 22 and a plurality of cell culturing chambers 24 positioned in a retention well 25. A supply conduit 26 made of flexible or rubber tubing is used to supply medium 18 from reservoir 12 to the pumping section 20. The pumping section 20 is preferably a multi-channel peristaltic pumping unit which provides the motive force for delivering individual streams of medium through individual sections of tubing 28 to the culture chambers 24.

The heating and gassing section 22 heats the medium to a preselected temperature and adds gas to the medium through the tubing walls. The medium flows through the culture chamber containing the cells, perifuses the cells, and then carries away the waste components produced by the cells, such as lactic acid, and any useful product secreted by the cells through tubing sections 29. The tubing sections 29 are fluidly connected to a manifold section of tubing 30 which provides a return for the waste and product containing medium through a common return tubing line 32 into the reservoir 12.

The particular culture chamber 24 that is used with the present invention is not important. Preferably, the culture chamber is a hollow fiber cartridge device, such as is described in U.S. patent application entitled "Method and Device for Culturing Cells," Ser. No. 789,649, filed on Oct. 21, 1985 by Martinez et al and assigned to the same assignee as the present application and which is hereby incorporated by reference, or which is described in the Knazek et al U.S. Pat. Nos. 3,821,087 and 3,883,393, or a closed-end loop-type culturing chamber sold by MicroGon of Laguna Hills, Calif., or any similar type of culturing chamber in which cells are cultured by perifusion.

The culturing chambers contain hollow fibers that retain the cells being cultured while permitting the medium and any secretory products produced to flow through the walls of the fibers. An illustrative example of a suitable pore size is a 2,000,000 molecular weight cutoff.

In addition, cells of the appropriate type could be allowed to grow in the cell culturing loop or in the reservoir without being constrained in any type of culturing chamber. However, the cells should be restricted from the medium waste removal and concentrating loop 16. Because of high shear that is produced by a back pressure mechanism (described subsequently), cells which enter the loop 16 could be damaged. Furthermore, it is generally desirable to have the cells separated from the product, when harvesting the product.

The culturing loop 14 also includes a bypass tubing section 34, a two-position three-way valve 36. The two-position three-way valve 36 is positioned at a fluid junction 39 of the tubing section 34 with the tubing 26. The two-position three-way valve includes pinch valve component 40 positioned to pinch the tubing 26 upstream of the junction 39 and pinch valve component 42 to pinch the tubing 34 upstream of the junction 39. During normal operation wherein medium is circulated from the reservoir 12 through the culturing loop 14, the valve component 40 is open and the valve component 42 is closed. During a waste removal cycle or a product concentration cycle wherein waste is being removed and the product is being concentrated, the bypass line 34 may be activated to isolate the cell culturing chambers in a recirculation loop that bypasses the reservoir. To activate the bypass line 34, the valve 40 is closed, while the valve 42 is open, recirculating medium through the culturing loop by way of the bypass tubing 34 while preventing flow of the medium from and to the reservoir 12. The exact valving mechanism to produce the recirculation loop that bypasses reservoir, is not important. For example, two separate two-way valves could be used along with bypass tubing section 34 to produce the same results as the two-position three-way valve 36.

The culturing loop 14 also includes an innoculation port 44 which is used to innoculate the culturing chambers 24 with cells at the beginning of a culturing cycle. Once the culturing chambers are innoculated, medium is passed through the culturing chambers to maintain and grow the cells.

A first sampling port 46 is included on the supply conduit 26 so that medium being supplied to the culture chambers may be sampled and analyzed. A second sample port 48 is included on the return line 30 of the culturing loop so that medium leaving the culture chambers may be sampled and analyzed.

The waste removal and concentration loop 16 includes a hollow fiber cartridge 50, a mechanism 52 for producing a back pressure within the hollow fiber cartridge, a pump 54 for providing motive force to transfer medium 18 from the reservoir 12 and through the loop 16 and back to the reservoir, and a supply medium tubing line 56 for removing medium from the reservoir and a return tubing line 58 for returning medium back to the reservoir.

The hollow fiber cartridge 50 is of a type having an outer shell 59 and an inlet end 60 and an outlet end 62 and a plurality of hollow fiber membranes (not shown) having semipermeable membrane walls potted proximate the ends 60 and 62 which is well known in the art. Suitable hollow fiber cartridges are commercially available by such companies as Erika Inc., a division of National Medical Care of Rockleigh, N.J. and CD Medical, Inc. of Miami Lakes, Fl., or the cartridge 50 may be of the type described in U.S. patent application entitled "Method and Device for culturing Cells," Ser. No. 789,649, filed on Oct. 21, 1985 by Martinez et al and assigned to the same assignee as the present application.

The hollow fibers of the cartridge 50 are of a porosity that permits waste components to pass through the membrane walls while retaining larger components such as product produced by the cells having a molecular weight of greater than 6,000. The cartridge 50 also contains a port 76 in fluid communication with the space in the cartridge between the shell and the hollow fibers and is fluidly connected to a tubing line 78. The line 78 is used to remove permeate containing the waste components Once back pressure produced by the back pressure mechanism is stopped, permeate flow stops even if pump 54 continues to run.

The pump 54 is preferably a bellows-type pump that is well known and includes an inlet end 64 and an outlet end 66. The pump 54 is preferably located on an upstream side of the hollow fiber cartridge 50 and pumps medium from the reservoir 12 through the hollow fiber cartridge 50.

The mechanism for producing back pressure 52 includes an end portion 68 of the return line 58, a line restriction 70, such as an orifice for restricting flow, and a bypass conduit 72 made of a tubing section with a pinch-type valve 74 for pinching the tubing.

A harvesting tubing line 82 is fluidly connected to the line portion 68 between the orifice 70 and the line 72. A pinch-type valve 84 is positioned to operate on the tubing line 82 for selectively closing and opening the line 82. The harvesting line 82 is preferably positioned between the back pressure mechanism 52 and the cartridge 50 to use the back pressure to provide a force to expell product-containing medium through line 78. The line 78, however, could be positioned anywhere along the loop 16 or in the reservoir using a separate pump to force product-containing medium through line 78.

Figure 3:
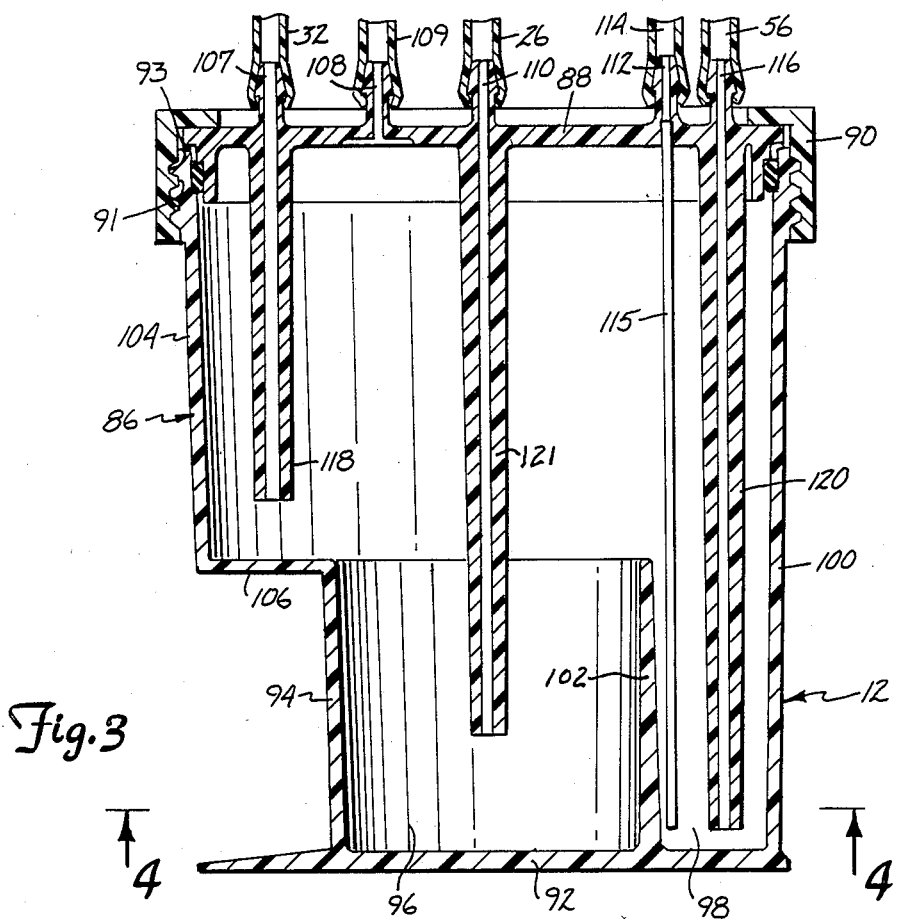
FIG. 3 is a cross-sectional view of the medium reservoir.
Figure 4:
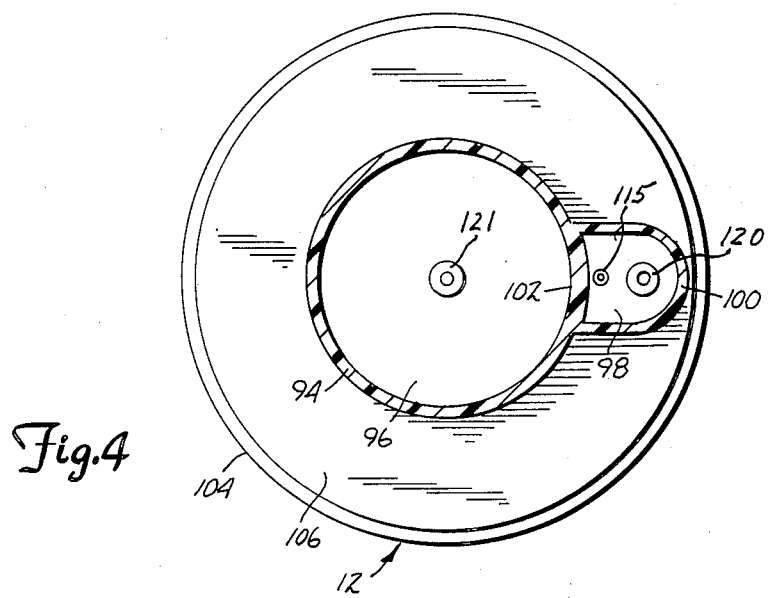
FIG. 4 is a sectional view taken along the line 4—4 in FIG. 3.

The reservoir 12 includes a fluid-retaining housing 86, a cover 88 and a securing lid 90 to secure the cover onto the housing 86 as illustrated in FIG. 3. The housing 86 contains a bottom wall 92. A vertical lower side wall portion 94 extends upwardly from the bottom wall 92 forming a lower primary medium-retaining chamber 96. A secondary medium retention chamber 98 is formed by a wall 100 which is joined at a weir section 102 of the wall 94. The weir section 102 extends upwardly only a portion of the height of the housing 86. The housing also includes an upper primary medium-retaining wall 104 which is joined to the walls 94 and 100 by a shoulder wall section 106.

The cover 88 includes a plurality of tubing connectors that extend above the cover 88. The tubing connectors include a tubing connector 107 for connection with the common return line 32, a tubing connector 108 which is connected to a vent line 109, a tubing connector 110 which is connected to the supply line 26, a tubing connector 112 is connected to a level sensor line 114, and a tubing connector 116 which is connected to the supply line 56. A return conduit 118 in fluid connection with the connector 107 extends downwardly into the housing ending above the shoulder wall section 106 of the housing. A supply conduit 121 in fluid connection with the connector 110 extends downwardly into the primary lower medium-retaining section 96. The connector 112 is positioned over the secondary medium-retaining section 98. A supply conduit 120 is in fluid connection with the connector 116 and extends downwardly into the secondary medium-retaining section 98.

The lid 90 includes threads 91 and the housing 86 includes threads 93 for engagement to secure the cover 88 in place.

A level sensor 122, diagrammatically illustrated in FIG. 2, senses the level of medium in the reservoir through the line 114. A section of stainless steel tubing 115 is in fluid communication with the connector 112 and extends downwardly into the secondary medium-retaining section 98. The level sensor 122 used in a working embodiment of the present invention is a pressure sensor wherein an air flow is provided through the line 114 and the tubing 115 and the backpressure is measured to obtain a reading of the level. However, other types of level sensors are included within the present invention that accomplish the same purpose, that is, measuring the amount of medium within the reservoir.

The supply tubing 120 is also positioned in the secondary medium-retaining section 98 preventing all of the medium from being withdrawn from the reservoir 12 during a harvesting cycle or a waste removal cycle. The level sensor 122 is disposed within the secondary medium-retaining section 98 to provide an alert when substantially most of the medium has been withdrawn from the reservoir. The weir section 102 prevents all of the medium being withdrawn from the reservoir and protects the cells being cultured in the culturing chambers 24 if the culturing loop 14 is being operated during a waste removal or a concentration product cycle.

When the waste product level in the medium reaches a level that is deleterious to the cells, the pump 54 is started to remove medium 18 from the reservoir 12 and pump the medium through the lumens of the hollow fibers in the cartridge 50. Simultaneously, the valve 74 is placed in a closed position with medium permitted to flow only through the orifice 70. The orifice 70 is sufficiently small to cause a back pressure within the lumens of the hollow fibers in the cartridge to aid in the transfer of waste components across the fiber walls. In the waste removal cycle, the check valve 80 is opened and the waste product flows from the cartridge 50 through the line 78.

The loop 16 can also be used to harvest any useful product produced by the cells such as an immunoglobulin. The harvesting can occur during each waste removal cycle by opening the valve 84 and permitting product-containing medium to flow through line 82. However, it is preferred that the product be further concentrated unless it has a deleterious effect on the cells within the culturing chambers 24. Consequently, harvesting does not typically occur during every waste removal cycle. Harvesting occurs at a predetermined product concentration level which depends on how the cell being cultured is affected by product concentration levels. When the product reaches the predetermined concentration within the medium, the pinch valve 74 is placed in the closed position and the pinch valve 84 is placed in the open position. The pump 54 pumps medium from the reservoir 12 and the product is collected through line 82. The pinch valve 80 may be opened during the harvesting cycle to remove the waste components.

During the harvesting cycle, the culturing loop 14 is typically closed off from the reservoir 12 by placing valve element 42 in an open position and valve element 40 in a closed position thereby creating a secondary culturing loop 130 that bypasses the reservoir 12 as illustrated in FIG. 2. The secondary culturing loop 130 is retained in operation until the medium level within the reservoir 12 is returned to its normal position. The culturing loop 130 protects the cells being cultured in the culturing chambers 24 from high concentrations of product or waste or higher osmotic pressure which exists within the reservoir during the harvesting cycle or the waste removal cycle. However, if it is desired to subject the cells to such concentration levels, the culturing loop 130 is omitted. When it is desired to return to the culturing loop 14 that draws medium from the reservoir 12, the valve component 42 is placed in a closed position, and the valve component 40 is placed in an open position.

A medium replenishment pump 132 is included to replenish medium drawn off, especially after the concentration cycle. The medium replenishment pump 132 is preferably fluidly connected to the supply line 56 by a line 134 upstream of the cartridge 50. Positioning the medium replenishment pump 132 upstream of the cartridge 50 permits fresh medium to flow through the lumens of the cartridge 50, scrubbing any high molecular weight components that have been retained on interior surfaces of the fibers. During medium replenishment, the valve 74 is open to provide the highest flow rate possible through the loop 16. However, the medium pump 132 may be positioned anywhere in the apparatus if desired.

A factor pump 136 is positioned on the return line 30 of the culturing loop 14 and is fluidly connected to the line 30 by a line 138. The factor pump 136 provides secondary factors to the medium, such as glucose, serum, and the like, depending on need. The factor pump may be operated during the waste removal cycle wherein glucose and other low molecular weight substances are removed along with the waste component. The factor pump is also operable during a harvesting cycle when high molecular weight proteins and serum needed by the cells are drawn off with the product and must be replenished.

The various pumps and valves may be placed in operation manually to provide the sequence that is desired with the particular cells being cultured. However, it is preferred that the valves and pumps are operated through a suitable microprocessor or microprocessors (not shown) the use of which to operate valves and pumps in cell culturing devices is well known in the art.

In summary, the apparatus of the present invention provides for a method to culture cells, remove waste components from the culturing medium, concentrate product within the medium, and replenish medium as needed along with adding any secondary factors that may be needed by the cells. The apparatus provides versatility in that the cell culturing loop may be isolated if the waste component level or product level is deleterious to the cells being cultured. In addition, the present invention keeps higher molecular weight components of the medium along with the product while removing only low molecular weight materials in the waste removal cycle, thus reducing the necessity of adding high molecular weight serum components and eliminating the need for a separate separation of the product from high molecular weight components in the medium.

Although the present invention has been described with reference to preferred embodiments, workers skilled in the art will recognize that changes may be made in form and detail without departing from the spirit and scope of the invention.

What is claimed is:

1. A cell culturing apparatus comprising:
   reservoir means for retaining a supply of fluid medium;
   a first medium circulating loop in fluid communication with the reservoir means and in which cells are being cultured in the fluid medium and having first means for transporting the medium from the reservoir means and back to the reservoir means; and
   a second medium circulating loop in fluid communication with the reservoir means including means for removing waste components from the medium and for concentrating cell products within the medium including:
   second means for transporting the medium from the reservoir means and back to the reservoir means in fluid communication with the reservoir means;
   mass transfer means having a semipermeable membrane permitting selective transfer of the waste components from the medium and for retaining cell products within the medium in fluid communication with the second means for transporting so that medium flows along one side of the membrane;
   flow restriction means in fluid communication with the first conduit means and a first bypass means selectively positionable in a closed and open position such that when in the closed and open position the medium is forced to flow through the flow restriction means creating a back pressure in the mass transfer means; and
   means for removing concentrated product and medium comprising a product harvest line with a second valving means positionable to close and open the harvest line wherein the means for removal is in fluid communication with the first conduit means in position downstream of the first bypass means and upstream of the flow restriction means.

2. The apparatus of claim 1 wherein the second means for transporting the medium includes first conduit means wherein medium is drawn from the reservoir means and including pumping means in fluid communication with the first conduit means for providing motive force for transporting the medium through the mass transfer means.

3. The apparatus of claim 2 wherein the pumping means is located upstream from the mass transfer means.

4. The apparatus of claim 1 wherein the mass transfer means is a hollow fiber cartridge in fluid communication with the first conduit means.

5. The apparatus of claim 4 wherein the hollow fiber cartridge has a port that is fluidly connected to a waste removal line.

6. The apparatus of claim 1 and further including medium replenishment means including first pumping means in fluid communication with the first conduit means upstream of the mass transfer means for replenishment of medium removed from the apparatus.

7. The apparatus of claim 2 wherein the reservoir means includes a medium-retaining housing having a side wall, a bottom wall, and a weir extending upwardly from the bottom wall, the weir and the side wall forming a secondary medium-retaining section and level sensing means extending into the secondary medium-retaining section.

8. The apparatus of claim 7 wherein the first conduit means has a suction end portion disposed within the secondary medium-retaining section.

9. The apparatus of claim 8 wherein the first medium circulating loop has a suction end portion disposed outside the secondary medium-retaining section in the reservoir means.

10. The apparatus of claim 1 wherein the first medium circulating loop includes a cell culturing means, first conduit means fluidly connecting the culturing means with the reservoir means for providing a passage for medium from the reservoir means to the culturing means and second conduit means fluidly connecting the culturing means with the reservoir means and providing a passage for return of the medium from the culturing means to the reservoir means and a bypass means for selectively bypassing the reservoir means and having third conduit means with one end in fluid communication with the first conduit means and another end in fluid communication with the second conduit means and a third valve means for selectively providing flow through the third conduit means and for selectively shutting off flow in the third conduit means.

11. The apparatus of claim 10 wherein the third valve means includes a first valve component positioned to selectively restrict and permit flow of medium in the first conduit means upstream of the fluid connection between the first conduit means and the third conduit means and a second valve component positioned to selectively restrict and permit flow in the third conduit means.

12. The apparatus of claim 11 and further including second pumping means in fluid communication with the second conduit means for providing medium replenishment to the reservoir means.

13. A cell culturing apparatus comprising:
   reservoir means for retaining a supply of fluid medium including a medium retaining housing having a side wall, a bottom wall, and a weir extending upwardly from the bottom wall, the weir and the side wall forming a secondary medium retaining section and level sensing means extending into the secondary medium retaining section;

a first medium circulating loop in fluid communication with the reservoir means and in which cells are being cultured in the fluid medium and having first means for transporting the medium from the reservoir means and back to the reservoir means; and a second medium circulating loop in fluid communication with the reservoir means including means for removing waste component from the medium and for concentrating cell products within the medium including:

mass transfer means having a semi-permeable membrane permitting selective transfer of the waste components from the medium and for retaining cell products within the medium in fluid communication with the second means for transporting so that medium flows along one side of the membrane;

a second means for transporting the medium comprising a first conduit means wherein the medium is drawn from the reservoir means and including a pumping means in fluid communication with the first conduit means for providing motive force for transporting the medium through the mass transfer means; and means for selectively producing a back pressure in the mass transfer means such that the waste components are forced to transfer through the membrane.

14. The apparatus of claim 13 wherein the first conduit means has a suction end portion disposed within the secondary medium retaining section.

15. The apparatus of claim 14 wherein the first medium circulating loop has a suction end portion disposed outside the secondary medium retaining section in the reservoir means.

16. Cell culturing apparatus comprising:

reservoir means for retaining a supply of fluid to the medium;

a first medium circulating loop comprising a cell culturing means, a first conduit means fluidly connecting the culturing means with the reservoir means for providing a passage for medium from the reservoir means to the culturing means and a second conduit means fluidly connecting the culturing means with the reservoir means and providing a passage for return of the medium from the culturing means to the reservoir means and a bypass means for selectively bypassing the reservoir means and having a third conduit means with one end in fluid communication with the first conduit means and another end in fluid communication with the second conduit means and a third valve means for selectively providing flow through the third conduit means and for selectively shutting off the flow in the third conduit means; and a second medium circulating loop in fluid communication with the reservoir means including means for removing waste components from the medium and for concentrating cell products within the medium including:

second means for transporting the medium from the reservoir means and back to the reservoir means in fluid communication with the reservoir means;

mass transfer means having a semi-permeable membrane permitting selective transfer of the waste components for the medium and for retaining cell products within the medium in fluid communication with the second means for transporting so that the medium flows along one side of the membrane; and means for selectively producing a back pressure in the mass transfer means such that the waste components are forced to transfer through the membrane.

17. The apparatus of claim 16 wherein the third valve means include a first valve component positioned to selectively restrict and permit flow of medium in the first conduit means upstream of the fluid connection between the first conduit means and the third conduit means and a second valve component positioned to selectively restrict and permit flow in the third conduit means.

18. The apparatus of claim 17 and further including second pumping means in fluid communication with the second conduit means for providing medium replenishment to the reservoir means.

* * * * *